(12) United States Patent
Enyart et al.

(10) Patent No.: US 8,092,837 B2
(45) Date of Patent: Jan. 10, 2012

(54) FIBRIN BASED GLUE WITH FUNCTIONALIZED HYDROPHILIC POLYMER PROTEIN BINDING AGENT

(75) Inventors: Hillary Enyart, Warsaw, IN (US); Jacy Hoeppner, Warsaw, IN (US); Mike Leach, Warsaw, IN (US); Shon Steger, Warsaw, IN (US); Sona Sundaramurthy, Warsaw, IN (US)

(73) Assignee: Biomet Manufacturing Corp, Warsaw, IN (US)

(*) Notice: Subject to any disclaimer, the term of this patent is extended or adjusted under 35 U.S.C. 154(b) by 1017 days.

(21) Appl. No.: 11/741,333

(22) Filed: Apr. 27, 2007

(65) Prior Publication Data

US 2008/0267902 A1 Oct. 30, 2008

(51) Int. Cl.
*A61K 31/74* (2006.01)
*A61K 35/16* (2006.01)

(52) U.S. Cl. .............................. 424/530; 424/78.08

(58) Field of Classification Search .................. None
See application file for complete search history.

(56) References Cited

U.S. PATENT DOCUMENTS

| | | | |
|---|---|---|---|
| 4,839,345 A | 6/1989 | Doi et al. | |
| 5,292,362 A | 3/1994 | Bass et al. | |
| 5,514,379 A | 5/1996 | Weissleder et al. | |
| 5,583,114 A | 12/1996 | Barrows et al. | |
| 5,733,563 A | 3/1998 | Fortier | |
| 6,010,627 A * | 1/2000 | Hood, III | 210/321.6 |
| 6,051,248 A | 4/2000 | Sawhney et al. | |
| 6,096,309 A * | 8/2000 | Prior et al. | 424/94.63 |
| 6,150,327 A | 11/2000 | Sinn et al. | |
| 6,274,090 B1 | 8/2001 | Coelho et al. | |
| 6,312,725 B1 * | 11/2001 | Wallace et al. | 424/484 |
| 6,371,975 B2 | 4/2002 | Cruise et al. | |
| 6,458,147 B1 | 10/2002 | Cruise et al. | |
| 6,472,162 B1 | 10/2002 | Coelho et al. | |
| 6,706,690 B2 | 3/2004 | Reich et al. | |
| 6,830,756 B2 | 12/2004 | Hnojewyj | |
| 6,899,889 B1 | 5/2005 | Hnojewyj et al. | |
| 6,905,612 B2 | 6/2005 | Dorian et al. | |
| 6,949,114 B2 | 9/2005 | Milo et al. | |
| 6,994,686 B2 | 2/2006 | Cruise et al. | |
| 7,056,722 B1 | 6/2006 | Coelho et al. | |
| 2001/0031948 A1 | 10/2001 | Cruise et al. | |
| 2002/0161399 A1 | 10/2002 | Cruise et al. | |
| 2003/0100921 A1 | 5/2003 | Addis et al. | |
| 2005/0085858 A1 | 4/2005 | Hnojewyj | |
| 2006/0024371 A1 | 2/2006 | Hnojewyj et al. | |
| 2006/0088570 A1 | 4/2006 | Cruise et al. | |

FOREIGN PATENT DOCUMENTS

| | | | |
|---|---|---|---|
| EP | 0 341 007 | * | 8/1989 |
| EP | 1263327 B1 | | 8/2005 |
| EP | 1107813 B1 | | 5/2006 |
| WO | WO 98/12274 A1 | | 3/1998 |
| WO | WO 00/12018 A1 | | 3/2000 |
| WO | WO 01/66017 A1 | | 9/2001 |
| WO | WO 02/064186 A2 | | 8/2002 |
| WO | WO 02/064186 A3 | | 8/2002 |
| WO | WO 02/064187 A2 | | 8/2002 |
| WO | WO 02/064187 A3 | | 8/2002 |
| WO | WO 2005/061018 A1 | | 7/2005 |

* cited by examiner

*Primary Examiner* — Sandra Saucier
(74) *Attorney, Agent, or Firm* — Taft, Stettinius & Hollister, LLP; Ryan O. White

(57) ABSTRACT

The present invention provides a non-liquid biomaterial that may be used as a surgical sealant, a suture support, a blood flow controller, an adhesion reducing agent, an adhesion preventing agent, a tissue support, a tissue filler, a wound dressing or a combination thereof. The non-liquid biomaterial may comprise a blood derived material such as plasma, platelet poor plasma, platelet rich plasma or a material derived from blood containing tissue aspirate, such as bone marrow aspirate, a protein binding agent and a polymerizing agent. Methods for making and using the non-liquid biomaterial are also provided.

17 Claims, No Drawings

FIBRIN BASED GLUE WITH FUNCTIONALIZED HYDROPHILIC POLYMER PROTEIN BINDING AGENT

BACKGROUND OF THE INVENTION

The present invention relates generally to blood products with a binding agent and more particularly to solutions of blood products with a protein binding agent that, when mixed with a hemostatic agent, form a non-liquid material.

Biological glues are used in a number of different applications, such as controlling blood leaks during surgical procedures or for procedures such as angioplasty. Biological glues may also be used for prevention of adhesions as a wound heals, for filling tissue voids or to augment healing. Addition of cellular, biological or pharmaceutical agents to the biological glue or the use of a scaffold with the biological glue may augment the performance of biological glues for specific applications.

Among the best known of biological glues are fibrin-based glues. Fibrin based glues take advantage of the physiological properties of fibrin, namely that the conversion of fibrinogen to fibrin produces a stable fibrin clot. One major advantage of fibrin-based glues is that they may be autologous, using a patient's own blood as the source of the fibrinogen in the fibrin-based glue. However, one problem in using plasma or blood, particularly when concentrated to produce an increased fibrinogen concentration, is the presence of albumin. Some testing has suggested that plasma concentrates attain a maximum mechanical strength at about 3-fold concentration. After reaching this point, the material may become increasingly tacky with minimal increase in cohesion. It is thought that the albumin present with the fibrinogen is partially responsible for this mechanical behavior.

Thus it would be desirable to have a fibrin-based glue that has increased mechanical strength compared to existing blood derived fibrin glues. It would be further desirable to have a more cohesive fibrin-based glue that is not tacky, or for which the degree of tackiness can be controlled by altering the formulation to suit the desired application.

SUMMARY OF THE INVENTION

In one aspect of the present invention there is provided a non-liquid biomaterial comprising a blood product solution comprising a blood derived material and a protein binding agent, the protein binding agent having a functionality of at least two, a polymerizing agent and wherein upon mixing the blood product solution and the polymerizing agent the non-liquid biomaterial is formed. The blood derived material may be at least partially derived from whole blood, from materials derived from whole blood, or from blood containing tissue aspirates or their derivatives such as, but not limited to, bone marrow aspirate. The blood derived material may be plasma, concentrated plasma, platelet rich plasma, platelet poor plasma, blood, bone marrow aspirate, concentrated cells from bone marrow aspirate with plasma, or combinations thereof. The non-liquid biomaterial may be used as a surgical sealant, a suture support, a blood flow controller, an adhesion reducing agent, an adhesion preventing agent, a tissue support, a tissue filler, a tissue or cell scaffold, a wound dressing or a combination thereof.

In another aspect of the present invention there is provided a non-liquid biomaterial comprising a plasma solution comprising a plasma product and a protein binding agent, wherein the protein binding agent is a hydrophilic polymer having a functionality of at least two, a hemostatic agent and wherein the non-liquid biomaterial is formed upon mixing the plasma solution and the hemostatic agent.

In a further aspect of the present invention there is provided a method for producing a non-liquid biomaterial comprising mixing a blood derived material and a protein binding agent to produce a blood product solution, wherein the protein binding agent has a functionality of at least two, and mixing the blood product solution with a polymerizing agent to form the non-liquid biomaterial. The method may further comprise filtering at least one of the blood derived material or the blood product solution prior to mixing the blood product solution with the polymerizing agent. Alternatively or additionally, the method may comprise concentrating the blood derived material, wherein the blood derived material is concentrated from about 1-fold to about 8-fold.

In yet another aspect of the present invention there is provided a method for producing a non-liquid biomaterial from a concentrated plasma product comprising introducing the plasma product into a plasma-concentrating device, the device comprising a protein binding agent having a functionality of at least two, mixing the plasma product with the protein binding agent in the plasma-concentrating device, forming a plasma solution, concentrating the plasma solution, removing the concentrated plasma solution from the plasma-concentrating device and mixing the concentrated plasma solution with a hemostatic agent to form the non-liquid biomaterial. The method may further comprise mixing the plasma product with the protein binding agent in a first chamber of the plasma-concentrating device, forming a plasma solution, filtering the plasma solution through a filter separating the first chamber from a second chamber and concentrating the plasma solution in the second chamber. Alternatively or additionally, the method may further comprise placing whole anti-coagulated blood or bone marrow aspirate into a device for separating the plasma product from whole blood, obtaining the plasma product from the blood and removing the plasma product from the device before placing the plasma product in the plasma-concentrating device.

In another aspect of the present invention there is provided a method for producing a non-liquid biomaterial from a plasma product comprising placing whole blood or bone marrow aspirate into a first chamber of a blood separating device, separating the plasma product from the whole blood into a second chamber of the blood separating device, wherein the second chamber comprises a protein binding agent having a functionality of at least 2, mixing the plasma product and the protein binding agent in the second chamber, forming a plasma solution, removing the plasma solution from the blood separating device and mixing the plasma solution with a hemostatic agent to form a non-liquid biomaterial.

In a further aspect of the present invention there is provided a method of applying a non-liquid biomaterial to a patient undergoing a surgical procedure comprising drawing whole blood or bone marrow aspirate from the patient either before or during the procedure, isolating at least one blood derived material from the whole blood or bone marrow aspirate, mixing the blood derived material with a protein binding agent with a functionality of at least two, forming a blood product solution, mixing the blood product solution with a polymerizing agent to form a non-liquid biomaterial either in situ at the site of the surgical procedure or ex situ and then delivered to the site of the surgical procedure.

These and other features, aspects and advantages of the present invention will become better understood with reference to the following description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides a non-liquid biomaterial which may comprise a blood product solution and a polymerizing agent where the non-liquid biomaterial may be formed by mixing the blood product solution with the polymerizing agent. The blood product solution may comprise a blood derived material and a protein binding agent where the blood derived material may be blood, bone marrow aspirate or a plasma product such as plasma, platelet poor plasma, platelet rich plasma. The protein binding agent may have a functionality of at least two where the functional groups may allow for covalent binding of the protein binding agent to proteins in the blood product solution. The binding of the protein binding agent to the proteins may increase the mechanical strength, decrease or eliminate any tackiness and provides a fibrin glue with superior handling properties. The non-liquid biomaterial of the present invention may be used as a surgical sealant, a suture support, a blood flow controller, an adhesion reducing agent, an adhesion preventing agent, a tissue support, a tissue filler, a tissue or cell scaffold or a wound dressing.

In one embodiment, the non-liquid biomaterial may comprise a blood product solution and a polymerizing agent where the non-liquid biomaterial may be formed by mixing the blood product solution with the polymerizing agent. The blood product solution may comprise a blood derived material and a protein binding agent having a functionality of at least two. In an illustrative embodiment, the blood derived material may be, but not limited to, blood, bone marrow aspirate, concentrated cells from bone marrow aspirate with plasma, a plasma product such as plasma, concentrated plasma, platelet rich plasma, platelet poor plasma, or combinations thereof. It will be appreciated that the blood derived material may be derived from sources other than whole blood such as, but not limited to, blood containing aspirates. The blood derived material may be at least partially derived from whole blood, from materials derived from whole blood, or from blood containing tissue aspirates or their derivatives, a non-limiting example of which is bone marrow aspirate. The blood derived material from tissue aspirates may comprise additional cells from the tissue aspirated. A non-limiting example may be stem cells from bone marrow aspirate. The blood derived material may be autologous or allogeneic. The advantages of using autologous materials are well known in the art, including decreased risk of an adverse immunogenic reaction and/or exposure to tainted or diseased blood derived materials.

The blood derived material may be used at physiological concentrations or it may be concentrated. In one illustrative embodiment the blood derived material is concentrated from 1-fold to about 8-fold. In another illustrative embodiment, the blood derived material is concentrated from about 1.5-fold to about 4-fold. Concentrating the blood derived material may increase fibrinogen concentration which may in turn, result in a non-liquid biomaterial with increased mechanical strength. Alternatively, the blood product solution may be concentrated instead of or in addition to the blood derived material. In one illustrative embodiment, the blood derived material may be mixed with the protein binding agent to form the blood product solution and the blood product solution may then be concentrated by, for example, from about 1-fold to about 8-fold or from about 1.5-fold to about 4-fold.

The blood derived material or the blood product solution may be concentrated by any method known in the art. In one illustrative embodiment, the blood derived material or the blood product solution may be concentrated using a centrifugal concentrator such as those described in U.S. patent application Ser. Nos. 11/342,982 and 11/342,761, both of which are incorporated by reference herein. In an alternative illustrative embodiment, the blood derived material or the blood product solution may be concentrated in a bead containing chamber system such as that described in U.S. Pat. No. 6,905,612 (incorporated by reference herein).

The blood derived material may further comprise an anticoagulant. The presence of an anticoagulant would prevent the blood derived material from forming a non-liquid biomaterial prior to being mixed with the polymerizing agent. It may also be desirable to add an anticoagulant for some methods of isolating a plasma product from whole blood. One device for separating whole blood into various components is described in U.S. patent application Ser. No. 11/442,631 (incorporated by reference herein). There are also a number of systems commercially available that may allow for rapid production of plasma from whole blood. Non-limiting examples may be GPS®II or Vortech™. These systems allow for the rapid production of plasma and subsequently the non-liquid biomaterial of the present invention during surgery or other medical procedures.

It may also be desirable to add $Ca^{2+}$ or another material that counteracts any anticoagulants that may be present in the blood product solution. The Ca2+ may be added to the blood product solution or the polymerizing agent. In one embodiment, the source of the $Ca^{2+}$ is a calcium salt. Such materials are well known in the art. In an illustrative embodiment, the polymerizing agent is in a $CaCl_2$ solution.

In another embodiment, the blood derived material may be mixed with a protein binding agent where the protein binding agent has a functionality of at least two. The protein binding agent may be in the form of a liquid or a solid when mixed with the blood derived material. In an illustrative embodiment, the protein binding agent has a functionality of from about 2 to about 4. In an additional illustrative embodiment, the protein binding agent has a functionality of from about 2 to about 8. The functionality is an expression of the number of functional groups found on the protein binding agent available to interact with proteins in the blood derived material. While not necessary, it may be desirable to have functional groups that preferentially interact with proteins other than fibrinogen. Alternately, if the protein binding agent binds to fibrinogen it may bind in such a way as not to inhibit the conversion of fibrinogen to fibrin.

The functional groups may be selected to selectively react with thiols, amines or they may be non-specific. Functional groups that react with thiols may be, but not limited to, vinyl sulfone, N-ethyl maleimide, iodoacetamide and orthopyridyl disulfide. Alternatively, functional groups that specifically react with amines may be, but not limited to, aldehydes. Functional groups that are non-selective may be, but not limited to, active esters, epoxides, carbonylimidazole, nitrophenyl carbonates, tresylate, mesylate, tosylate and isocyanate. In an illustrative embodiment, the functional groups of the protein binding agents may be capable of binding to free amino groups of the proteins of the blood derived materials. By way of non-limiting example, serum albumin has a significant number of lysine residues. Similarly, other blood proteins, including immunoglobulins, may have lysine residues available for binding. Therefore it may be desirable to have a protein binding agent with functional groups that can bind to the available lysine residues of serum albumin or other common blood proteins. In an exemplary embodiment, the functional group may be an ester of N-hydroxysuccinimide.

In a further embodiment, the protein binding agent may be a hydrophilic biocompatible polymer. Non-limiting examples of hydrophilic biocompatible polymers that may be used in the present invention may be poly(ethylene glycol), poly(ethylene oxide), poly(vinyl alcohol), poly(vinylpyrrolidine), poly(ethyloxazoline), poly(ethylene glycol)-co-poly (propylene glycol) block polymers or combinations thereof. In an exemplary embodiment, the hydrophilic polymer may be poly(ethylene glycol) or poly(ethylene oxide). Additionally, the polymer may be linear or it may be multi-armed (multi-branched). In an illustrative embodiment, a multi-armed polymer may comprise at least three arms. In another illustrative embodiment, a multi-armed polymer may have from about 3 to about 8 arms. In a further illustrative embodiment, the protein binding agent may comprise a 4-arm poly (ethylene glycol) succinimidyl glutarate or a 4-arm poly(ethylene oxide) succinimidyl glutarate.

The protein binding agent may have a molecular weight of from about 1,000 to about 30,000. In an illustrative embodiment, the protein binding agent may have a molecular weight of from about 10,000 to about 25,000.

The concentration of the protein binding agent with respect to the blood product solution may be dependent on the nature of the protein binding agent, including the functionality and the reactivity of the functional groups and/or the concentration of the blood derived material and/or the blood product solution. In one illustrative embodiment, the concentration of protein binding agent may be from about 0.25 mg/ml to about 10 mg/ml with respect to the blood product solution. In another illustrative embodiment, the concentration of the protein binding solution may be from about 1 mg/ml to about 5 mg/ml. It is well within the ability of the skilled artisan to determine the optimal amount of protein binding agent without undue experimentation.

In a further embodiment, the blood product solution is mixed with a polymerizing agent to produce the non-liquid biomaterial of the present invention. A non-liquid material may be any material that is not a true fluid as determined by the naked eye. Non-liquid materials may be, but not limited to solids, gels, hydrogels or semi-solids. The polymerizing agent may catalyze the formation of the non-liquid biomaterial or it may be an integral part of the biomaterial. Non-limiting examples of polymerizing agents that may be an integral part of the non-liquid biomaterial may be cross-linking agents. Alternatively, non-limiting examples of polymerizing agents that catalyze the formation of the non-liquid biomaterial may be hemostatic agents. Hemostatic agents may activate the clotting cascade in blood derived materials of the blood product solution. Additionally, hemostatic agents may activate platelets. In one illustrative example, the hemostatic agent may catalyze the conversion of fibrinogen to fibrin. Non-limiting examples of hemostatic agents may be gelatin sponges, collagen sponges, microfibrillar collagen, thrombin or venom derived factors such as reptilase or batroxobin. The thrombin may be autologous thrombin, xenogenic thrombin, recombinant human thrombin or a combination of these. Autologous thrombin may be obtained using a thrombin processing device such as, but not limited to, the TPD™ device. Such devices are disclosed in U.S. Pat. Nos. 6,274,090, 6,472,162 and 7,056,722, all of which are incorporated by reference herein.

The amount or concentration of polymerizing agent will vary based on the reagent, the blood product solution and the desired time period for forming the non-liquid material. For example, in surgical applications a vascular surgeon may want rapid formation of the non-liquid biomaterial in order to stop bleeding. In an exemplary embodiment, the non-liquid biomaterial of the present invention is formed in no greater than one minute. Alternatively, a reconstructive surgeon, for example, may want a slower formation of the non-liquid material to give time to reposition a flap or a graft. The skilled artisan may be able, without undue experimentation, determine the amount of polymerization agent needed for the desired application. In one exemplary embodiment, the hemostatic agent may be thrombin and may be from about 10 U/ml to about 1000 U/ml with respect to the blood product solution. Alternatively, the thrombin may be from about 50 U/ml to about 200 U/ml with respect to blood product solution.

In one embodiment, the non-liquid biomaterial may comprise pharmaceutical or biological agents. Non-limiting examples of pharmaceutical agents may be, but not limited to, antibiotics such as, but not limited to, gentamicin, tobramycin, minocycline, rifampin, vancomycin, bacitracin, a combination of minocycline and rifampin, or combinations thereof. Other non-limiting examples of pharmaceutical agents may be, but not limited to, antibacterials such as, but not limited to, silver, while quinolones, oxazolidinones, sulfa drugs or combinations thereof. Non-limiting examples of biological agents may be, but not limited to, growth factors such as, but not limited to, FGFs, VEGF, PDGF, GDFs, CDGFs or combinations thereof, or bone morphogenic proteins such as, but not limited to, BMP 2, BMP 4, BMP 5, BMP 6, BMP 7, BMP 12, BMP 14, BMP 15, heterodimers thereof or combinations thereof. Alternatively, the non-liquid biomaterial may comprise cells. In one exemplary embodiment, the cells may be tissue regenerative cells such as, but not limited to, chondrocytes, osteoprogenitor cells, endothelial cells, endothelial progenitor cells, epithelial cells, cardiomyocytes, dermatocytes, smooth muscle cells and combinations thereof. Alternatively, the cells may comprise, but not be limited to stem cells, osteoblasts, fibroblasts, erythrocytes, leukocytes, adipocytes or combinations thereof.

In another embodiment, the pharmaceutical agents, biological agents or cells may be added to any of the components that form the non-liquid biomaterial. For example, the pharmaceutical agents, biological agents or cells may be added to the blood derived material, the blood product solution, the protein binding agent or the polymerizing agent. Alternatively, the cells may be from the tissue aspirate and be present in the blood derived material. In an illustrative embodiment, cells, such as bone marrow derived stem cells, may be derived from blood containing tissue aspirate while a blood derived material, such as plasma, may also be derived from the same blood containing tissue aspirate. Alternatively, the pharmaceutical agents, biological agents and cells may be exogenous to the non-liquid biomaterial and its components. In an alternate illustrative embodiment cells, such as bone marrow derived stem cells, may be derived from bone marrow aspirate whereas the blood derived material, such as, but not limited to, plasma, may be derived from whole blood.

In one embodiment, the non-liquid biomaterial may be integrated with at least a portion of a porous scaffold. The porous scaffold may comprise a plurality of pores. Additionally, the porous scaffold may comprise calcium, a biocompatible resorbable or semi-resorbable polymer, collagen, processed bone, biocompatible metal or a combination thereof. The non-liquid material may be formed within at least a portion of the pores of the porous scaffold. In an exemplary embodiment, the porous scaffold may be a tissue or cell scaffold through which cellular ingrowth may occur over time and in which the scaffold may be integrated with or replaced by a body tissue. In another exemplary embodiment, the porous scaffold may be a tissue support where it may comprise a characteristic mechanical property designed to mimic, augment or replace all or a portion of a body tissue. In a further exemplary embodiment, the porous scaffold may be present on a surface of an implantable device. In all of the exemplary embodiments it is contemplated that the non-liquid biomaterial of the present invention may be used in combination with the porous scaffold either as a therapeutic agent, as a fixative agent or both.

Methods for making the non-liquid biomaterial of the present invention are also provided. In one embodiment, a blood derived material and a protein binding agent having a functionality of at least two are mixed together to form a blood product solution. The protein binding agent may be added to the blood derived material as a solid, suspension or solution. The blood derived material and protein binding agent may be mixed by any means known in the art. In one illustrative embodiment, the blood derived material may be drawn up into a syringe that comprises the protein binding agent. The blood derived material and the protein binding agent may then be mixed by transfer between two syringes, forming the blood product solution. Alternatively, the blood derived material and the protein binding agent may be mixed in a container by mechanical stirring means, agitation and/or ultrasound.

In another embodiment, the blood derived material and/or the blood product solution may be used at physiological concentrations or they may be concentrated. In one illustrative embodiment the blood derived material is concentrated from 1-fold to about 8-fold. In another illustrative embodiment, the blood derived material is concentrated from about 1.5-fold to about 4-fold.

The blood derived material or the blood product solution may be concentrated by any method known in the art. In one illustrative embodiment, the blood derived material or the blood product solution may be concentrated in a concentration device such as a centrifugal concentrator. Examples of centrifugal concentrators are described in U.S. patent application Ser. Nos. 11/342,982 and 11/342,761, both of which are incorporated by reference herein. In an alternative illustrative embodiment, the blood derived material or the blood product solution may be concentrated in a bead containing chamber system such as that described in U.S. Pat. No. 6,905,612 (incorporated by reference herein).

In a further embodiment, the blood derived material may be a plasma product such as, but not limited to plasma, platelet poor plasma or platelet rich plasma. The plasma product may be concentrated and the methods of the present invention may further comprise introducing the plasma product into a plasma concentrating device such as those listed above. In an exemplary embodiment, the plasma product is introduced into a plasma concentrating device such as, but not limited to, Plasmax™. In another exemplary embodiment, the device comprises the protein binding agent within a first chamber where the plasma product is introduced. The plasma product and protein binding agent may then be mixed together to form a plasma solution. The plasma solution may then be concentrated in the device. In an illustrative embodiment, the device may comprise a plurality of beads capable of concentrating the plasma product. A non-limiting example of such beads may be dehydrated concentrator gel beads for removing water from the plasma solution, thereby concentrating the plasma solution. The plasma solution may be concentrated from about 1-fold to about 8-fold or from about 1.5-fold to about 4-fold. After concentration, the plasma solution may be removed from the device and mixed with a hemostatic agent to form the non-liquid biomaterial.

In all the embodiments described for the present invention, removing the blood product solution or plasma solution from a device may comprise removing the blood product solution or plasma solution to either a separate discrete device or into a delivery device before being mixed with the polymerizing agent. In an exemplary embodiment, the blood product solution or plasma solution may be removed from a device into a delivery device such as mixing tip where the mixing tip is connected to a syringe or other containing comprising the polymerizing agent.

In another embodiment, the blood derived material and/or the blood product solution may be filtered prior to mixing the blood product solution with the polymerizing agent. The filter may be such that one or more of particulate matter, concentrating beads, or proteins are removed. In an illustrative embodiment, the filter may be from 0.1 μm to about 100 μm or from about 1 μm to about 50 μm. In another illustrative embodiment, if a concentrated blood product solution is desired, after introducing the blood derived material into the concentrating device, the blood derived material may be mixed with the protein binding agent in a first chamber of the plasma concentrating device, forming the blood product solution. The blood product solution may then be filtered into a second chamber through a filter separating the first chamber from a second chamber, where the blood product solution may be concentrated. It will be appreciated that the mixing with the protein binding agent, filtration and concentration may all be done in a single device. The concentrated plasma solution may be removed from the plasma concentrating device and mixed with a hemostatic agent to form the non-liquid biomaterial of the present invention.

In alternate embodiment, the concentrating device may comprise the protein binding agent in a second chamber, separate from the first chamber in which the blood derived material may be introduced. The blood derived material may then be filtered into the second chamber through a filter separating the first chamber from the second chamber. The filtered blood derived material may be mixed with the protein binding agent in the second chamber to provide the blood product solution. The blood product solution may be concentrated and removed from the concentration device and mixed with a hemostatic agent to form the non-liquid biomaterial of the present invention. Alternatively, the blood product solution may be filtered through a second filter into a third chamber either before or after being concentrated.

In another alternate embodiment, the blood derived material may be introduced into a first chamber of the concentrating device and subsequently it may be concentrated. After concentration, the concentrated blood derived material may be filtered into a second chamber of the concentrating device, where the second chamber may comprise the protein binding agent. The filtered concentrated blood derived material may be mixed with the protein binding agent in the second chamber to provide the blood product solution. The blood product solution may be concentrated and/or filtered before it may be removed from the concentration device and mixed with the polymerizing agent.

The methods of the present invention may further comprise obtaining plasma products from whole blood or bone marrow aspirate. In a further embodiment, whole anti-coagulated blood or bone marrow aspirate may be introduced into a device such as, but not limited to, the device described in U.S. patent application Ser. No. 11/442,631 that may be capable of separating out plasma products from whole blood. A commercial example of such a device may be GPS®II. The plasma product may be obtained from the blood or bone marrow aspirate, removed from the device and introduced into a device for concentrating plasma products. Alternatively, the plasma product may be used to make the non-liquid biomaterial of the present invention without concentration.

The non-liquid biomateral of the present invention may be applied to a patient during a surgical procedure. In such a case, it is contemplated that the non-liquid biomaterial may be made in the operating room during the surgical procedure. Alternatively, autologous or allogenic blood or bone marrow aspirate may be collected prior to the surgical procedure and the blood product solution or plasma solution may be prepared ahead of the surgery. In one embodiment, blood or bone marrow aspirate may be drawn from the patient either before or during the surgical procedure and a blood derived material may be isolated. The blood derived material may be isolated in a time frame beginning with the blood draw and ending with surgical application and formation of the non-liquid biomaterial. In one non-limiting example, the blood derived material may be isolated in a time frame lasting no longer than about one hour. In another non-limiting example, the blood derived material may be isolated in a time frame lasting no longer than about thirty minutes. The blood derived material may then be mixed with the protein binding agent as described herein to form a blood product solution or plasma solution. Either solution is then mixed with a polymerizing agent to form the non-liquid biomaterial at the site of the surgical procedure. The non-liquid biomaterial may be formed and delivered to the site using a static mixer, a tip or a nozzle. The blood product or plasma solution may be sprayed onto or applied by another method to the surgical site almost simultaneously with mixing with the polymerizing agent to be formed in situ. In an exemplary embodiment, the non-liquid material is formed no greater than one minute after mixing the blood product solution and the polymerizing agent. Alternatively, the non-liquid biomaterial may be formed ex situ and then applied to the surgical site. The non-liquid biomaterial may be used as a surgical sealant, a suture support, a blood flow controller, an adhesion reducing agent, an adhesion preventing agent, a tissue support, a tissue filler, a tissue or cell scaffold, a wound dressing or a combination thereof.

In an alternate embodiment, the non-liquid biomaterial may be applied with a porous scaffold. In an exemplary embodiment, the porous scaffold may be implanted at the surgical site and the non-liquid biomaterial may be subsequently delivered to the site where it may be integrated into at least a portion of the porous scaffold. In an alternate exemplary embodiment, the porous scaffold and the non-liquid biomaterial may be delivered to the surgical site concurrently where the non-liquid biomaterial may be integrated with at least a portion of the porous scaffold.

In one illustrative embodiment, the non-liquid biomaterial may be used as a hemostatic agent. If the desired use for the product is hemostasis the surgeon may choose to apply the product with a spray tip, an aerosol tip or a drip tip. A spray tip may usually be chosen for large, seeping areas of bleeding, while a drip tip may generally be chosen for smaller, more focused points of bleeding. After the processing of the blood, the blood product solution or plasma solution may be transferred to a delivery device. Before applying the product to the bleeding site, the site may be dried as much as possible. The surgeon may then apply the product with the appropriate tip.

In another illustrative embodiment, the non-liquid biomaterial of the present invention may be used for sealing of anastomoses. In addition to promoting healing, the non-liquid biomaterial may function as support to keep the fluid inside the channel from leaking outside the channel. For vascular anastomosis, the blood supply at the anastomosis site may be clamped off and the two ends of an anastomosis may be secured by suture. For intestinal anastomosis the bowel may be secured/clamped to prevent leakage. The newly positioned section of intestine or resected portion of intestine may be connected and sutured. After the securing of the anastomosis, the site may be dried as much as possible. After the blood product solution or plasma solution is formed, it may be transferred to a delivery device along with the polymerizing agent. A drip tip may be used to apply the blood product around the anastomosis. The product may be allowed time to reach sufficient strength before clamps are released.

In a further illustrative embodiment, the non-liquid biomaterial of the present invention may be used for the reduction of adhesions. The non-liquid biomaterial may function as a barrier between two layers of tissue to prevent them from scarring or healing together. Adhesions may be a risk in almost all surgeries, but the non-liquid biomaterial of the present invention may most commonly be used in spine, general and OBGYN surgeries to reduce adhesions. For these types of surgeries, it may be desired to cover a large area with the non-liquid biomaterial. This may be accomplished by using a spraying tip or nozzle, effectively delivering small droplets over a large area. Particularly with spine, limiting the thickness of the applied material may be desirable and is facilitated by a spraying tip.

In yet another illustrative embodiment, the non-liquid biomaterial of the present invention may be used as a surgical sealant. The function of the sealant may be to maintain a barrier and plug holes in a tissue. The surgical sealant function may overlap with hemostasis, anastomosis, or adhesion prevention applications. Among the most significant sealant applications may be dural repair (either cranial dura or spinal dura). Following cranial or spinal surgery, or in certain rare conditions, it may be common to have a tear or opening in the dura. To repair the dura, a sealant may be used to cover the site of application to prevent cerebrospinal fluid (CSF) from leaking through the openings in the dura and to support healing. In this application, the dural sealant may also be used to support sutures, as an adjunct to dural patches, or to seal holes around the suture through either dura or dural patches. A spray tip may be used for well dispersed coverage, though a more targeted approach (like a drip tip) may be used if a specific tear is targeted or the surgical exposure to the site is limited.

It should be understood, of course, that the foregoing relates to exemplary embodiments of the invention and that modifications may be made without departing from the spirit and scope of the invention as set forth in the following claims.

We claim:

1. A biomaterial comprising: a blood product mixture and a hemostatic agent comprising thrombin, the biomaterial being formed by initially mixing together a blood derived material and a hydrophilic polymer to form a blood product mixture, and then subsequently mixing the blood product mixture with the hemostatic agent comprising thrombin to form a non-liquid biomaterial;

wherein the hydrophilic polymer has a protein binding functionality of at least two and is selected from at least one of poly(ethylene glycol), poly(ethylene oxide), poly(vinyl alcohol), poly(vinylpyrrolidine), poly(ethyloxazoline, poly(ethylene glycol-co-poly(propylene glycol) block polymer, and copolymers or combinations thereof; and wherein the blood derived material is plasma, platelet rich plasma or platelet poor plasma.

2. The biomaterial of claim 1 wherein the thrombin is selected from at least one of autologous thrombin, xenogenic thrombin and recombinant thrombin and is present in an amount of from about 10 U/ml to about 1000 U/ml with respect to the blood product solution.

3. The biomaterial of claim 1 wherein the plasma, platelet rich plasma or platelet poor plasma is concentrated.

4. The biomaterial of claim 1 wherein the plasma, platelet rich plasma or platelet poor plasma is concentrated from about 1-fold to about 8-fold.

5. The biomaterial of claim 1 wherein the hydrophilic polymer has a molecular weight of from about 1,000 to about 30,000.

6. The biomaterial of claim 1 wherein the hydrophilic polymer comprises at least three arms.

7. The biomaterial of claim 1 wherein the hydrophilic polymer has a protein binding functionality from 2 to about 8.

8. The biomaterial of claim 1, wherein the protein binding functionality of the hydrophilic polymer comprises an ester or an aldehyde.

9. The biomaterial of claim 1, wherein the protein binding functionality of the hydrophilic polymer comprises an active ester of N-hydroxy succinimide.

10. The biomaterial of claim 1, wherein the hydrophilic polymer has a concentration of from about 0.25 mg/ml to about 10 tm/ml with respect to the blood derived material.

11. The biomaterial of claim 1 wherein the hemostatic agent converts fibrinogen in the blood derived material to fibrin.

12. The biomaterial of claim 1 wherein the hemostatic agent activates platelets.

13. The biomaterial of claim 1, wherein the blood derived material further comprises an anticoagulant; and wherein at least one of the blood product mixture or the hemostatic agent further comprises $Ca^{2+}$.

14. The biomaterial of claim 1 wherein the non-liquid biomaterial is formed within one minute after mixing the blood product solution and the hemostatic agent.

15. The biomaterial of claim 1 wherein the non-liquid biomaterial is a surgical sealant, a suture support, a blood flow controller, an adhesion reducing agent, an adhesion preventing agent, a tissue support, a tissue filler, a tissue or cell scaffold, a wound dressing or a combination thereof.

16. The biomaterial of claim 1 wherein the non-liquid biomaterial further comprises tissue regenerative cells.

17. The biomaterial of claim 1 wherein the non-liquid biomaterial comprises cells derived from tissue aspirate, stem cells, osteoblasts, fibroblasts, erythrocytes, leukocytes, adipocytes or combinations thereof.

* * * * *

UNITED STATES PATENT AND TRADEMARK OFFICE
CERTIFICATE OF CORRECTION

PATENT NO.        : 8,092,837 B2
APPLICATION NO.   : 11/741333
DATED             : January 10, 2012
INVENTOR(S)       : Hillary Enyart et al.

Page 1 of 1

It is certified that error appears in the above-identified patent and that said Letters Patent is hereby corrected as shown below:

Column 11, Claim 10, line 24, please change the term "tm/ml" to read "mg/ml"

Signed and Sealed this
Twenty-eighth Day of February, 2012

David J. Kappos
*Director of the United States Patent and Trademark Office*